US012573501B2

(12) United States Patent
Lenzenhuber et al.

(10) Patent No.: US 12,573,501 B2
(45) Date of Patent: Mar. 10, 2026

(54) SMART-PORT MULTIFUNCTIONAL READER/IDENTIFIER IN A PRODUCT STERILIZATION CYCLE

(71) Applicant: Aesculap AG, Tuttlingen (DE)

(72) Inventors: Frederick Lenzenhuber, Tuttlingen (DE); Roland-Alois Hoegerle, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 229 days.

(21) Appl. No.: 18/294,937

(22) PCT Filed: Aug. 2, 2022

(86) PCT No.: PCT/EP2022/071746
§ 371 (c)(1),
(2) Date: Feb. 2, 2024

(87) PCT Pub. No.: WO2023/012184
PCT Pub. Date: Feb. 9, 2023

(65) Prior Publication Data
US 2024/0339205 A1     Oct. 10, 2024

(30) Foreign Application Priority Data

Aug. 4, 2021     (DE) ..................... 10 2021 120 340.6

(51) Int. Cl.
*G16H 40/40*         (2018.01)
*A61B 90/96*         (2016.01)
(Continued)

(52) U.S. Cl.
CPC ............. *G16H 40/40* (2018.01); *A61B 90/96* (2016.02); *A61B 90/98* (2016.02); *G06K 7/0004* (2013.01); *G06V 10/255* (2022.01)

(58) Field of Classification Search
CPC ........ G16H 40/40; A61B 90/96; A61B 90/98; A61B 90/92; A61B 90/90; G06K 7/0004;
(Continued)

(56) References Cited

U.S. PATENT DOCUMENTS 9,501,671 B2    11/2016 Sun et al.
10,117,722 B2   11/2018 Sweeney
(Continued)

FOREIGN PATENT DOCUMENTS

CN      101848766 A     9/2010
CN      107563463 A     1/2018
(Continued)

OTHER PUBLICATIONS

Wei Liu et al. "Cognitive Tracking of Surgical Instruments Based on Stereo Vision and Depth Sensing." Proceeding of the IEEE International Conference on Robotics and Biomimetics (ROBIO) Shenzhen, China, Dec. 2013. (Year: 2013).*
(Continued)

*Primary Examiner* — Linh Giang Le
(74) *Attorney, Agent, or Firm* — Christopher A. Rothe; CM Law

(57)                ABSTRACT

A smart port can detect and read medical products using a multiplicity of modules. Each module is formed with a different detection technology. A system includes a smart port, a screen basket, and instrument holders. The instrument holders hold the medical products and can be introduced into the screen basket. A robot arm includes a smart port attached to or integrated in the robot arm. A device with artificial intelligence can be used for identifying and assessing medical products.

15 Claims, 8 Drawing Sheets

(51) Int. Cl.

| | | |
|---|---|---|
| *A61B 90/98* | (2016.01) | |
| *G06K 7/00* | (2006.01) | |
| *G06V 10/20* | (2022.01) | |

(58) Field of Classification Search

CPC ........... G06K 7/10118; G06K 7/10415; G06K 7/016; G06V 10/255

See application file for complete search history.

(56) References Cited

U.S. PATENT DOCUMENTS

| | | | |
|---|---|---|---|
| 10,321,972 | B2 | 6/2019 | Weinert et al. |
| 10,783,991 | B1 | 9/2020 | Laborde |
| 2007/0210159 | A1 | 9/2007 | Mott et al. |
| 2011/0156869 | A1 | 6/2011 | Watt |
| 2018/0214243 | A1 * | 8/2018 | Weinert ................. A61B 90/90 |

FOREIGN PATENT DOCUMENTS

| | | | | |
|---|---|---|---|---|
| DE | 102006056914 | A1 | 6/2008 | |
| DE | 102012107274 | A1 | 3/2014 | |
| EP | 0630820 | A1 | 6/1994 | |
| EP | 1402904 | A1 | 3/2004 | |
| EP | 2234032 | A2 | 9/2010 | |
| JP | 2008027268 | A | 2/2008 | |
| JP | 2015524326 | A | 8/2015 | |
| KR | 1020140100776 | | 8/2014 | |
| WO | 2010091838 | A2 | 8/2010 | |
| WO | WO-2019152563 | A1 * | 8/2019 | ................ B01L 3/54 |
| WO | 2020200975 | A1 | 10/2020 | |

OTHER PUBLICATIONS

Office Action received in Japanese Application No. 2024-506536 dated Jul. 29, 2024, with translation, 8 pages.

Office Action received in Chinese Application No. 202280054358.5 dated Dec. 21, 2024, with translation, 18 pages.

Communication under Rule 71 (3) EPC dated Nov. 29, 2023, with translation, 18 pages.

Search Report received in German Application No. 10 2021 120 340.6 dated Jun. 8, 2022, with translation, 15 pages.

Search Report received in International Application No. PCT/EP2022/071746 dated Feb. 3, 2023, with translation, 9 pages.

Written Opinion received in International Application No. PCT/EP2022/071746 dated Feb. 3, 2023, with translation, 19 pages.

* cited by examiner

SMART-PORT MULTIFUNCTIONAL READER/IDENTIFIER IN A PRODUCT STERILIZATION CYCLE

CROSS-REFERENCE TO RELATED APPLICATIONS

This application is the United States national stage entry of International Application No. PCT/EP2022/071746, filed on Aug. 2, 2022, and claims priority to German Application No. 10 2021 120 340.6, filed on Aug. 4, 2021. The contents of International Application No. PCT/EP2022/071746 and German Application No. 10 2021 120 340.6 are incorporated by reference herein in their entireties.

FIELD

The present disclosure relates to a smart port for detecting and reading medical products via a plurality of, preferably modular, modules, each of which is provided and configured with different detection technologies. The present disclosure further relates to a system comprising a smart port, a sieve basket and instrument holders insertable therein, which hold the medical products. Furthermore, the present disclosure relates to a robot arm with a smart port attached thereto or integrated therein and an apparatus with an artificial intelligence.

BACKGROUND

With a reading and/or writing device, product labels/product data carriers currently on the market can be read and, if necessary, written on by various medical products. Clinics currently have a wide variety of solutions for marking medical products.

The background to these product markings is that the sterilization cycle in a clinic, for example, should be traceable and verifiable to the best possible extent. Complete documentation on the whereabouts, wear, age, condition, maintenance, etc. enables clinics to prove that the medical products used were in perfect condition, for example in the event of injury of a patient.

Product labels such as article numbers and serial numbers are currently marked directly (manually) using a data matrix code (GTIN), also known as a QR code, a barcode and occasionally using RFID tags to detect. The latter are still very rarely used today, as the variety of tags/chips poses challenges for clinics. Each product labeling technology requires a separate reading and/or writing device, which in turn forwards information about the corresponding medical products to a plurality of instrument data management systems.

Medical products are understood to be, for example, surgical instruments and all products that need to be sterilized.

FIG. 1 shows medical products 2 of the current prior art manufactured in-house, which are equipped with NFC technology/an NFC tag 10 and can be read out via an intelligent control unit with and without a multiplexer. In addition, the NFC tags can be read out via a smart port 1 or a reading and/or writing device, which already provides an NFC interface 4 today.

Third-party medical products 2, on the other hand, have other technologies installed. These include, for example, the options shown in FIG. 1 under NFC technology, such as RFID-NFC, RDIF-LF, RFID-HF, RFID-UHF, RFID-SHF 11, and others, as bidirectional memory, but also a data matrix code 7, a barcode 8, quantum dots, and others, as fixed data memory. If applicable, cable connections are also conceivable, although these are not described further here.

In other words, this means that third-party medical products are logged via separate reading devices or suitable detection systems. This increases stocking of hardware and makes handling very complicated, so that training and instruction have to take place for each hardware.

EP 0 630 820 B1 discloses a method for monitoring the material flow during the preparation of sterile goods treatment, comprising the following steps: sterile goods are packed in a sterilization unit. Data characterizing the sterilization unit thus formed are recorded and stored on a data carrier connectable to the sterilization unit. The sterilization unit is sterilized in a sterilizer and the data characterizing the sterilization process is detected and registered. The data characterizing the sterilization unit is entered into a data processing device connected to the sterilizer. Depending on the data characterizing the sterilization unit, a suitable sterilization process is selected. The data characterizing the sterilization unit and the sterilization process are stored together.

U.S. Pat. No. 10,783,991 A1 describes a system comprising a plurality of RFID chips attached to a catheter, a data detection machine apparatus and a server apparatus. The data detection machine wirelessly transmits power to a first one of the RFID chips and receives first medical data from the first RFID chip while the first RFID chip is activated by the power receiver. The data detection apparatus generates a first message indicating the first medical data to be sent to the server apparatus. The server apparatus can determine aspects of the catheter such as position and risk conditions based on the first medical data.

EP 1 402 904 B1 describes a system for reprocessing medical instruments in a central sterilization department, wherein the instruments are provided with an identification code which is used in a packaging area of the sterilization department for packaging and screening and which is used to update a central database.

SUMMARY

Accordingly, the object of the present disclosure is to use a smart port or a multifunctional reading and/or writing device to avoid errors in the documentation and to reduce the time and effort required. Furthermore, it is the aim of the present disclosure that less hardware is required to detect one's own and third-party medical products.

Accordingly, the core of the disclosure is that the smart port/multifunctional reading and/or writing device for detecting and reading medical products is provided via a plurality of, preferably modular, modules, wherein the plurality of modules are each provided and configured with different detection technologies (possibly with different detection ranges with respect to each other).

In other words, this means that the smart port is a multifunctional device in which several different detection technologies can be integrated or are integrated. Such a smart port has the advantage that no additional reading devices for third-party/other medical products are required for reading and/or detecting. The smart port includes/comprises all necessary detection technologies, which are adapted to the various product markings.

Accordingly, the core invention consists in combining several technologies (different with respect to each other)

with each other in one device/apparatus, preferably with the use of artificial intelligence, in order to serve further-reaching applications.

Here, modules and future technologies are also described, which will also be established or could be established in the near future. In this way, the aim of the present disclosure is to cover almost all technologies with the smart port and to be able to serve all identification systems.

The present disclosure has the advantage of providing CSSD personnel with an easy-to-use reading and writing device. Handling is considerably simpler and space-saving due to compact hardware. Processes can be streamlined and optimized by using the smart port. In addition, less hardware is required and the key question regarding service life can be answered with the help of artificial intelligence. Cost savings are also possible through semi-automation and/or full automation.

It is preferred if the smart port defines a space around the smart port in which the medical products can be read. In other words, this means that a visual, three-dimensional space is created around the smart port, which is provided and configured to detect and read the medical products within this space.

It is advantageous if the smart port, in particular a computing unit of the smart port or in the smart port, is provided and configured to detect the medical products and to generate a signal within a predetermined and/or pre-defined time window, in particular within 2 to 3 seconds. The signal is provided to facilitate the logging of the detected medical products and to log the correct or incorrect assignment almost simultaneously with the detection of the medical product. It is advantageous here if the optical detection technology and the radio detection technology can be compared with each other within the time window in order to be able to guarantee the correctness of the assignment.

It is preferred if the smart port is provided and configured to output at least two different feedback signals, in particular optically and/or acoustically, whereby a correct or incorrect assignment can be recognized. The feedback signal for a correct assignment may be, for example, a short acoustic beep and/or green flashing of the smart port. An incorrect assignment may be announced with a longer or double beep and/or red flashing of the smart port.

According to a preferred embodiment, the smart port is preferably located in the central sterile services department (CSSD) and/or in the reprocessing unit for medical devices (RUMED) and/or the central sterile services department (CSSD) at a packing station or a central location where any medical product used is processed in a cycle anyway. In other words, this means that the medical products are viewed, maintained and assigned to a sieve basket at this location. All medical products that need to be reprocessed and sterilized pass through this point.

According to a preferred embodiment, the smart port is provided and configured to load detected and read-out data (itself) to a cloud-based infrastructure and to communicate with an instrument data management system of the customer and/or of the manufacturer via an interface. WLAN, UMTS, LORAWAN (Long Range Wide Area Network) or similar is preferably used for the transmission.

According to a further preferred embodiment, the individual modules used in the smart port may be used in modular form and omitted. At the same time, the smart port may also be equipped/extended with new/additional technologies.

According to a further preferred embodiment, a first module, preferably a scanner, is provided and configured to read a data matrix code and/or a barcode, which is provided and configured to be applied to a medical product and to be readable.

The data matrix code is a machine-readable code that is standard today. It is applied to medical products and contains GTIN (Global Trade Item Number) information. The device can handle all common data matrix codes.

The barcode is usually printed on a label and can be scanned and processed. The barcodes are also standardized.

The first module configured as a scanner is monodirectional/unidirectional. This means that the data content of the data matrix code and the barcode are only read. Further processing by an instrument management system (IMS) or an additional device is possible and provided.

According to a further preferred embodiment, a second module, preferably an RFID module, in particular an NFC module, is provided and configured to read at least one RFID tag, in particular at least one NFC tag, which is provided and configured to be accommodated in a medical product and to be readable and/or writable.

The NFC module is preferably provided and configured to read, process and also rewrite at least one NFC tag, which will be used in products in the future. For this purpose, it is advantageous if the medical products are placed very close to an antenna.

The RFID module is preferably provided and configured to read, process and also rewrite at least one RFID tag, which will be used in medical products in the future. It is advantageous here that medical products may be located in a wider environment than is possible with the NFC module. The distance has to be such that software can recognize the RSSI values of at least one RFID tag and can determine when an RFID tag is in the immediate vicinity. This is a variance.

The second module configured as an NFC module and/or RFID module is preferably configured bidirectionally. Accordingly, the data content of the NFC tag or of the RFID tag can be read and rewritten. Further processing by an integrated management system (IMS) or an additional device is possible and provided.

It is advantageous if the second module additionally or alternatively operates in a frequency range of HF, UHF and/or SHF. In this context, HF (High Frequency) is understood to mean a frequency of approximately 3 to 30 MHz, UHF (Ultra High Frequency) of approximately 0.3 to 3 GHz and SHF (Super High Frequency) of approximately 3 to 30 GHz.

According to a further preferred embodiment, a third module, preferably a LIDAR module, is provided and configured to perform surface scanning of at least one medical product. In other words, LIDAR can be used to scan surfaces in a similar way to radar or sonar. This has the advantage that it also works with very small installation sizes. LIDAR is based on light pulses and is used successfully in autonomous driving, among other things. This technology is provided to recognize medical products based on their geometry. At the same time, medical products can be compared with target states using this technology and any defects/deformations can be detected. Furthermore, the cutting edges of tools, for example, can be scanned to assess whether they are still intact or can no longer be used.

According to a further preferred embodiment, a fourth module, preferably an image detection module, is provided and configured to detect a medical product on the basis of at least one image. In other words, the fourth module can be used to recognize medical products based on their geometry. At the same time, medical products can be compared with target states using this technology and any defects/deformations can be detected. It is also possible, for example, to scan the cutting edges of tools and thus assess whether they are still intact or can no longer be used.

Furthermore, Lidar and camera may also be used to identify product categories. A DATA MATRIX code may also be read via the camera scan to record the serial number.

The article number and serial number are usually lasered onto products. This identification could also be read by a camera without the product containing a data carrier such as an RFID chip.

According to a preferred further development of the directly preceding two embodiments, artificial intelligence is provided in the third module and in the fourth module. Via the artificial intelligence, it is provided to perform and evaluate the comparison with a target state of a medical product and in this way to recognize any defects/deformations. In combination with the artificial intelligence, the present disclosure provides a tool for providing a direct answer to the question of service life.

In other words, artificial intelligence is preferably described in order to recognize products on the basis of their geometry and to enable product association with, if applicable, simultaneous assessment of the wear limits of medical products and the resulting disposal, renewal, revision, maintenance and/or new procurement. In particular, this makes it possible to assess the service life of medical products.

According to a further preferred embodiment, a fifth module, preferably a quantum dot sensor, is provided and configured to save data of a medical product via color differences. In other words, similar to a data matrix code, quantum dot sensors can be used to secure data via color differences and thus to perform identifications.

Furthermore, the disclosure relates to a system with a smart port, a sieve basket and instrument holders insertable therein, which hold the medical products, wherein the smart port is provided and configured to read out data and information of the at least one medical product in the sieve basket and/or the instrument holders and to transmit them to an instrument data management system of the customer, a cloud and/or to an instrument data management system of the manufacturer for further processing.

Furthermore, the present disclosure relates to a robot arm having a smart port attached thereto or integrated therein according to one of the preceding aspects. In other words, the smart port may be configured as a module attached to or integrally configured with a robot arm. Such a robot is used in the CSSD to automatically recognize medical products and read out data from medical products. This data is made available and passed on to another data processing unit.

One advantage is that it paves the way for a fully automated CSSD and therefore for saving costs. Entire reprocessing lines are planned here, which reprocess the medical products continuously—all day, all year round (24/7/365).

In addition, another preferred use of the smart port is as a data hub. In other words, the aim is to create a mesh network under the intelligent control unit so that they can communicate fully with each other and exchange data. In order to establish a solution that functions as a smart tray, the smart port is expanded to act as a central data hub, i.e. it collects the data from the intelligent control unit using BLE (Bluetooth) or other wireless technology and stores them in an in-house IMS and databases, or in a server-based or cloud-based or blockchain-based data storage solution.

This all happens as soon as an intelligent control unit comes within range of the smart port. That is, at least once in every reprocessing cycle. The data of the reprocessing cycle are cycle counts, article number, serial number, the cycles themselves, LifeCycleCounter and much more. This functionality is intended to also work bidirectionally. This means that all intelligent control units receive the same data status and are always updated when they arrive at the smart port.

A further preferred use of the present disclosure is provided as follows: today, consumables are delivered in sterile packaging, which then have to be detected. Similarly, there are individually packaged instruments in clinics, which are packaged and sterilized separately. The smart port is preferably provided and configured to scan the medical products through the sterile packaging without opening the sterile barrier.

In summary, the present disclosure serves the following key functions:

sterilization: in a sterile goods cycle, a central reading point/detection location, preferably at a central point, in particular the CSSD, is established in the hospital, which detects all medical products based on the use of all established technologies;

robotics: the path to semi-automated detection of medical products in the RUMED;

artificial intelligence: recognition of medical products using image recognition and system learning, in particular very small products such as diamond cutters with a diameter of 0.5 mm;

Furthermore, it is preferably provided in the present disclosure to equip the smart port with a number of two, three, four, five or more different modules in any desired combination.

It is further provided in the present disclosure that the smart port according to one of the preceding aspects is configured/provided for use as a detecting and reading apparatus of medical products.

DETAILED DESCRIPTION

Preferred configuration examples of the present disclosure are described below on the basis of the associated Figures.

Figure 1:
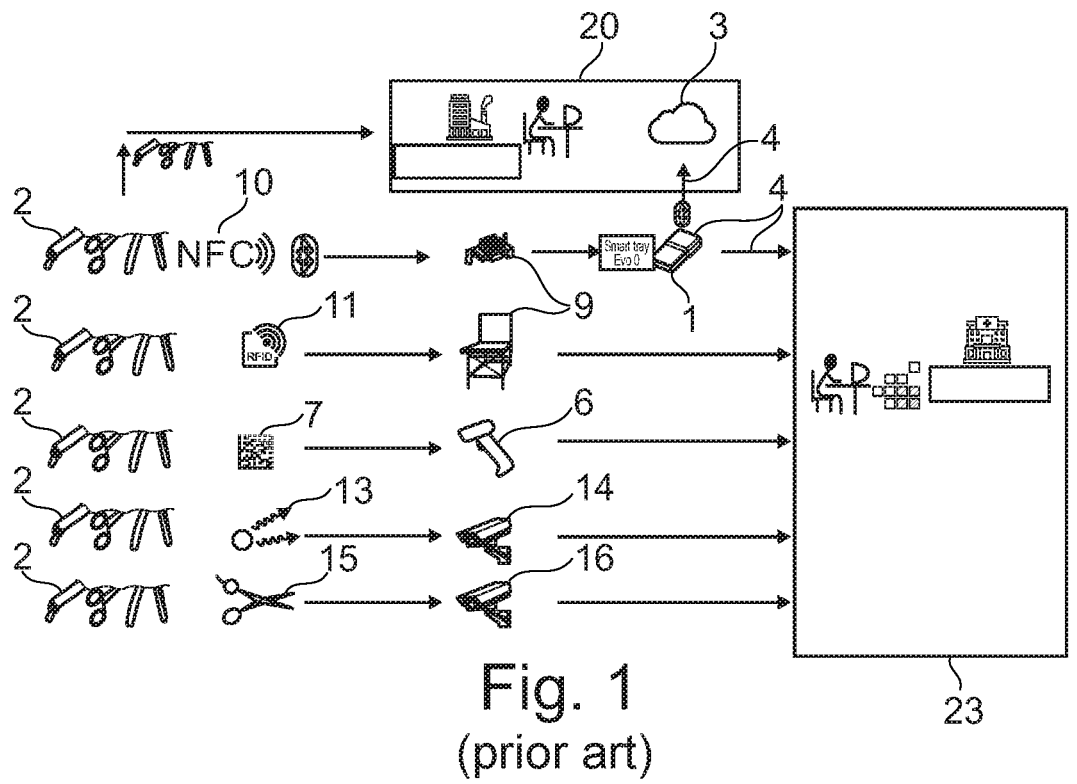
FIG. 1 is a representation for illustrating a reading system for medical products according to the prior art.

FIG. 1 has already been described above in the introduction to the description.

Figure 2:
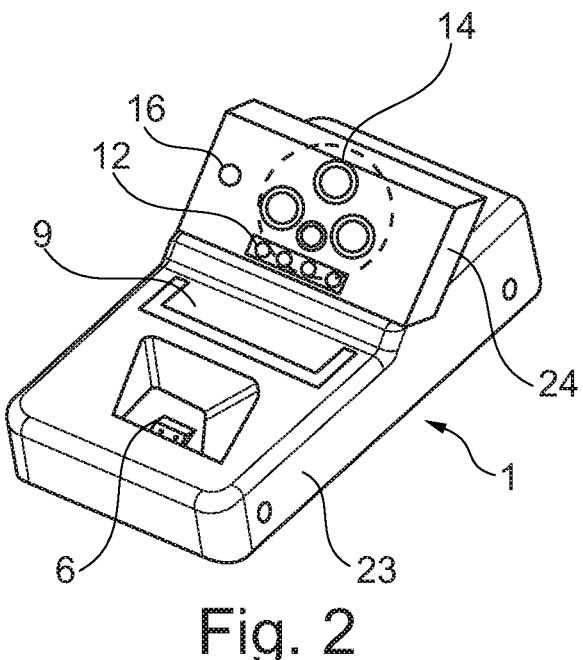
FIG. 2 is a representation of a smart port.

FIG. 2 is a representation of a smart port 1. In FIG. 2, the smart port 1/the multifunctional reading and writing device and its technologies are described in particular. The smart port 1 is only shown schematically and may also be configured differently in the modular structure. Accordingly, a schematic representation of the smart port 1 is shown in FIG. 2, in which all functions/detection technologies are combined. The individual modules may also be positioned in a different way if the ergonomic requirements make this necessary.

The smart port 1 has a first module 6, which is configured as a scanner and is provided to scan or read a barcode and/or a data matrix code or another 2D code. Furthermore, the smart port 1 has a second module 9, which is configured as an NFC module and/or RFID module and is provided to read at least one NFC tag 10 and/or at least one RFID tag 11 and, if applicable, to rewrite it. The smart port 1 has a third module 12, which performs surface scanning 13 via LIDAR and is provided to recognize and assess at least one medical product 2 on the basis of its geometry. In addition, the smart port 1 has a fourth module 14, which is configured as a camera system and which is provided to detect at least one image 15 of a medical product 2 and evaluate it using AI (artificial intelligence). The smart port 1 also has a fifth module 16, which is configured as a quantum dot sensor 27 and which is provided to detect data of a medical product 2 using color differences.

The shape of the smart port 1 may vary. In FIG. 2, the smart port 1 is configured with a rectangular housing 23. The first module 6 is set back in the housing 23, the second module 9 is located on the flat surface of the housing 23 and the third, fourth and fifth modules 12, 16 and 14 are integrated in an upward sloping structure 24.

Figures 3, 4:
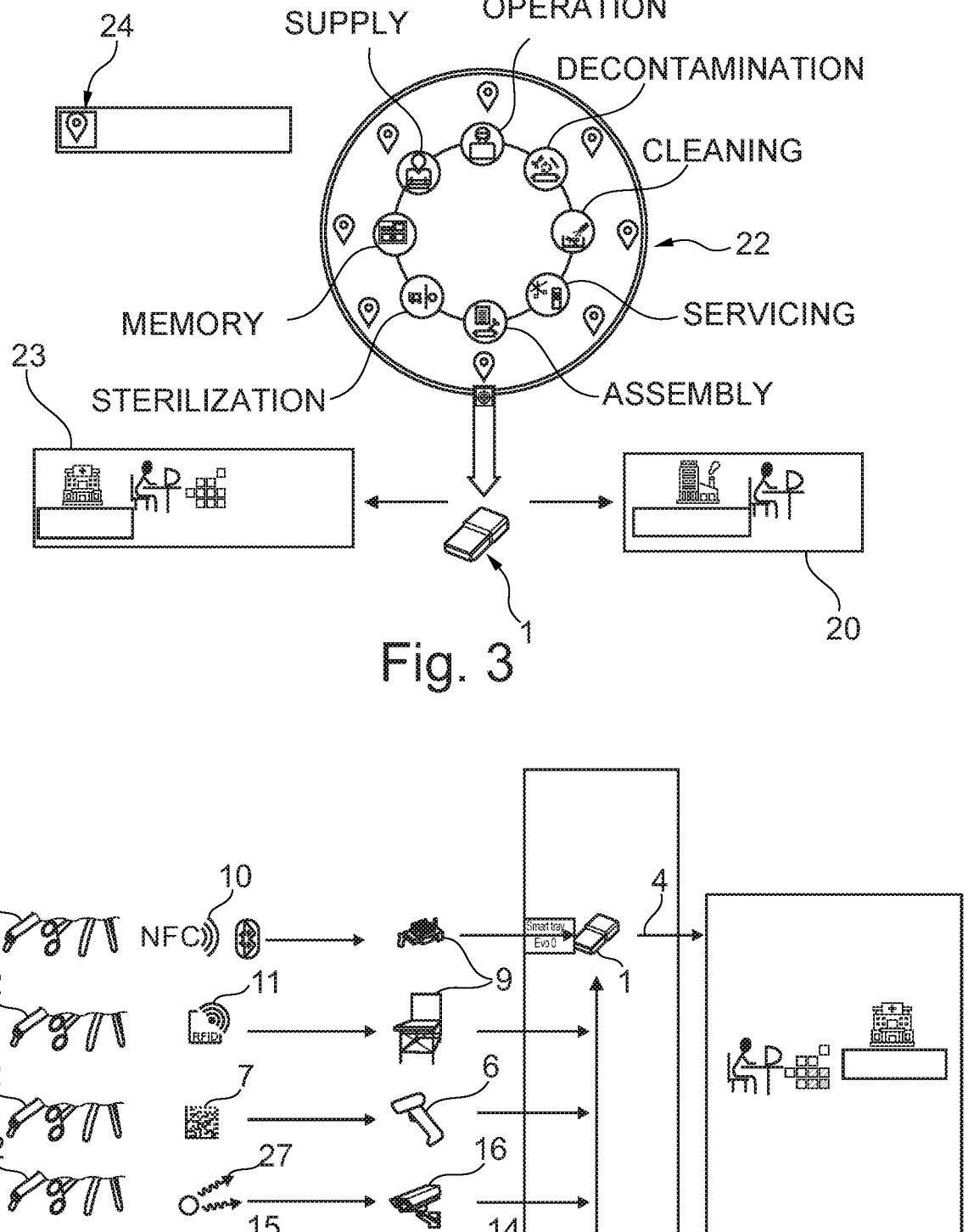
FIG. 3 is a representation of the positioning of the smart port.
FIG. 4 is a representation for illustrating a reading system for medical products with the smart port.

FIG. 3 is a representation of the positioning of the smart port 1. The smart port 1 is located at a packing station at which any medical product 2 used is processed in a cycle 22 anyway. Such a cycle 22 may be one of the following departments: CSSD, RUMED, etc. At this point, the medical products 2 are viewed, maintained and assigned to a sieve basket 18. The smart port 1 is configured to exchange data with the instrument data management system of the manufacturer 20 as well as with the instrument data management system of the customer 5. The location of the smart port 1 can be tracked as a tracking point 24.

FIG. 4 is a representation for illustrating a reading system for medical products 2 with the smart port 1. The smart port 1 is capable of covering all detection technologies. Via the modules 6, 9, 12, 14 and 16, which can be integrated in the smart port 1, it is possible to detect each medical product 2, regardless of the type of product marking, with exactly the one smart port 1 and to transfer the data on to an instrument data management system of the customer 5.

Figures 5, 6:
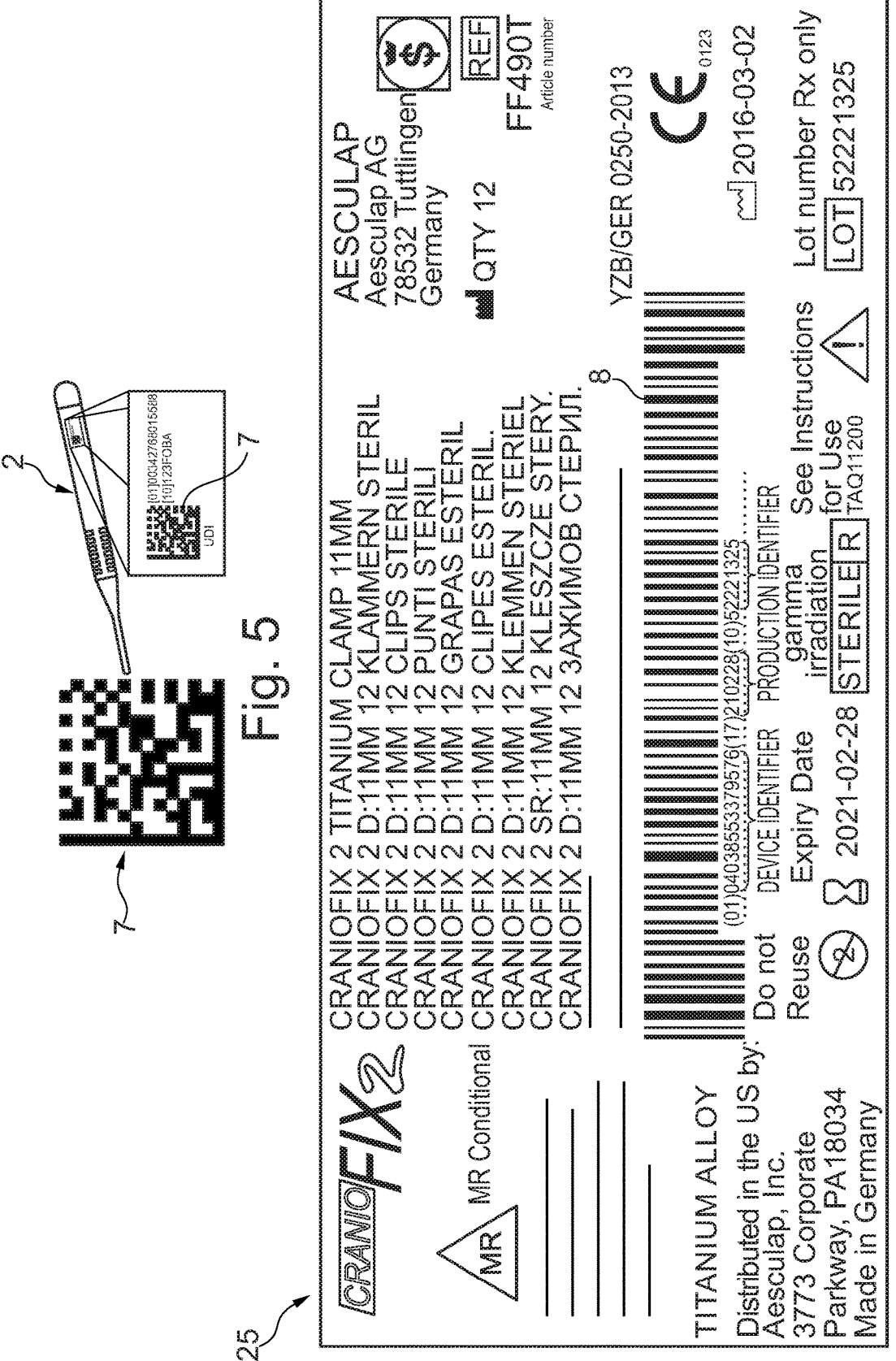
FIG. 5 is a representation of a data matrix code.
FIG. 6 is a representation of a barcode.

FIG. 5 is a representation of a data matrix code 7. The data matrix code 7 is attached to a medical product 2 in the right-hand half of FIG. 5 and can be read out via the first module 6 as shown in FIG. 2.

FIG. 6 is a representation of a barcode 8. The barcode 8 is provided to be printed on a label 25 and the label 25 is configured to be applied to a medical product 2.

Figure 7:
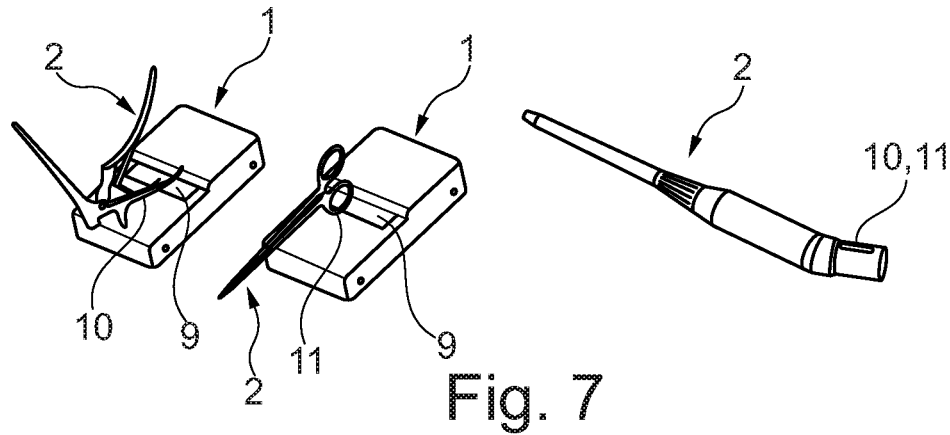
FIG. 7 is a representation of the second module with an NFC tag and an RFID tag.

FIG. 7 is a representation of the second module 9 with the NFC tag 10 and the RFID tag 11. Two smart ports 1 are shown in the left half of FIG. 7, one of which is shown as an example for detecting the NFC tag 10 and the other one for detecting the RFID tag 11 on a medical product 2 shown. In the right half of FIG. 7, an exemplary medical product 2 with the NFC tag 10 or the RFID tag 11 is shown as an example.

Figure 8:
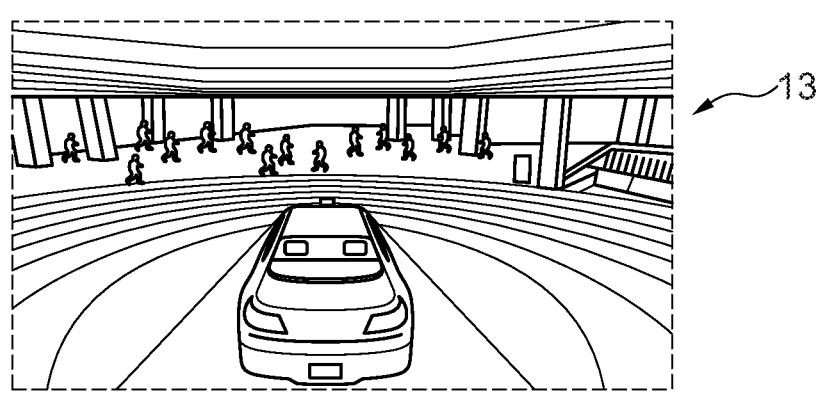
FIG. 8 is a representation of a performed surface scanning.

FIG. 8 is a representation of a surface scanning 13 performed with the third module 12 according to FIG. 2.

Figure 9:
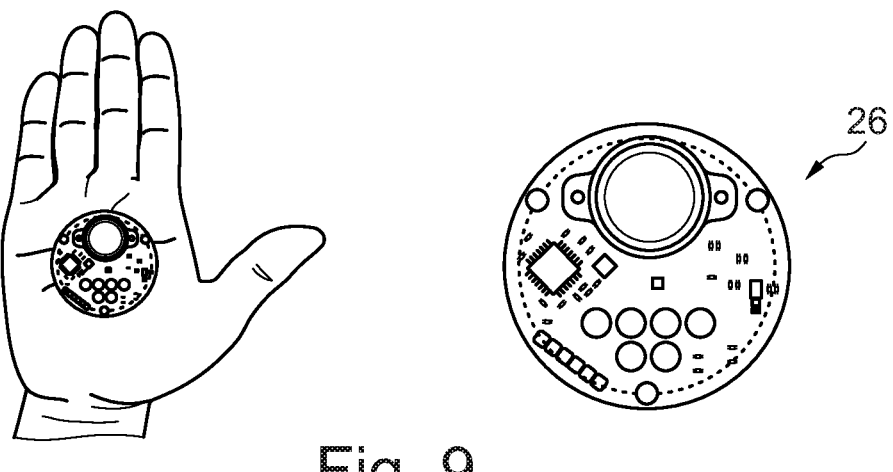
FIG. 9 shows the installation size and shape of a LIDAR sensor of the third module.

FIG. 9 shows the installation size and shape of a LIDAR sensor 26 of the third module 12 of the smart port 1. Here, the installation size of an exemplary LIDAR sensor 26 is approximately one-fifth of the palm of a hand.

Figure 10:
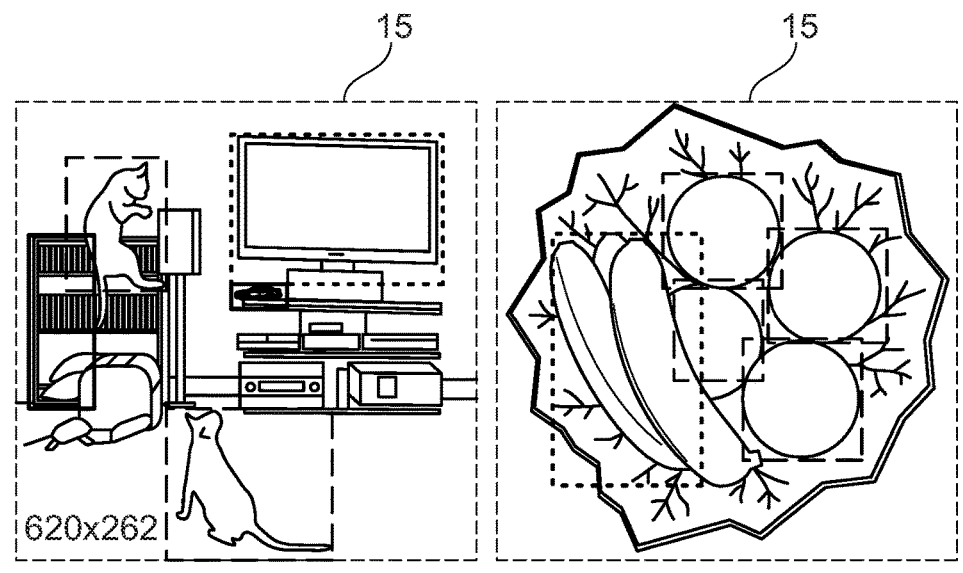
FIG. 10 is the representation of two detected images of the fourth module.

FIG. 10 is the representation of two detected images 15 of the fourth module 14 with different items, the recognition of which is indicated by a border.

Figure 11:
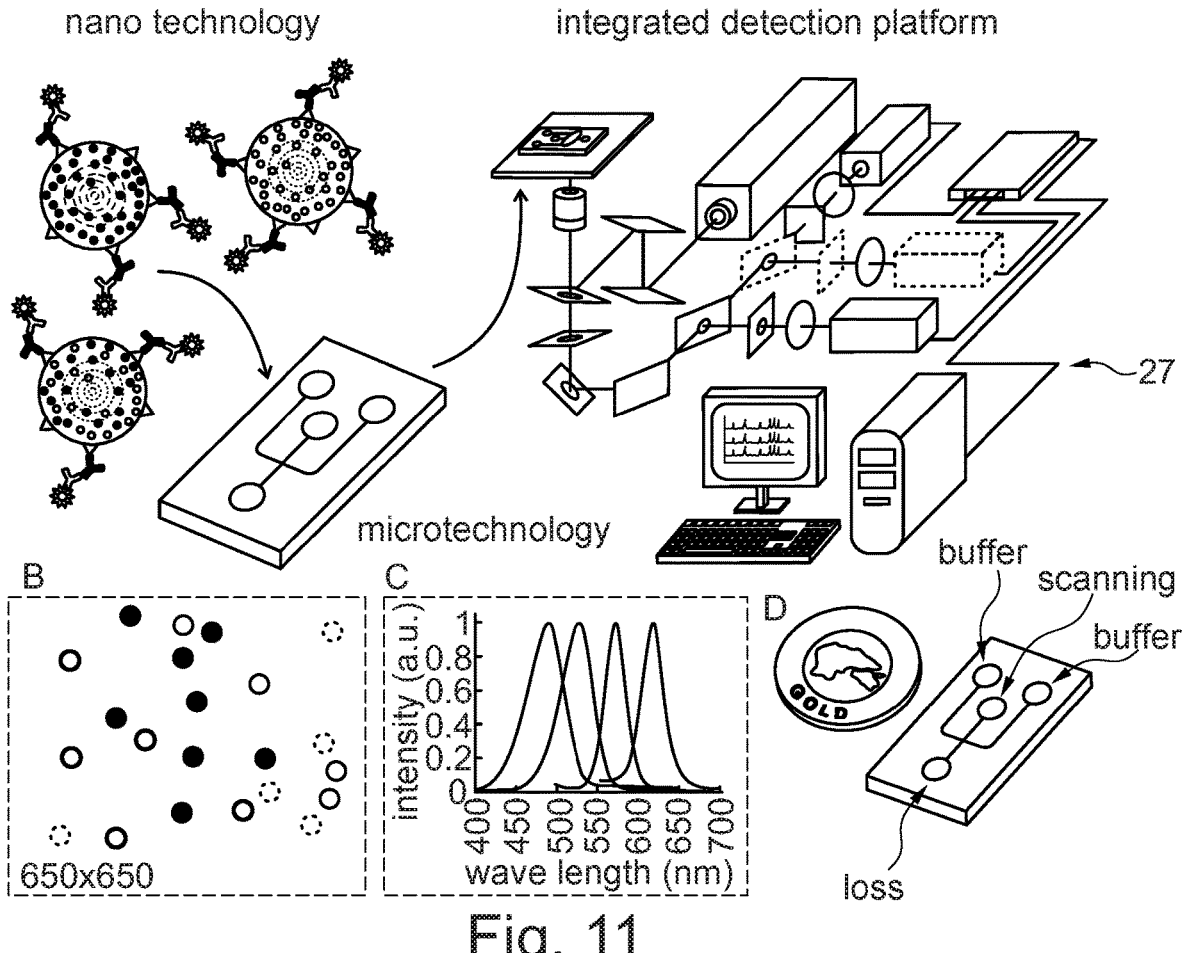
FIG. 11 is the representation of the QUANTUMDOT sensor of the fifth module.

FIG. 11 is the representation of the QUANTUMDOT sensor 27 of the fifth module 16.

Figure 12:
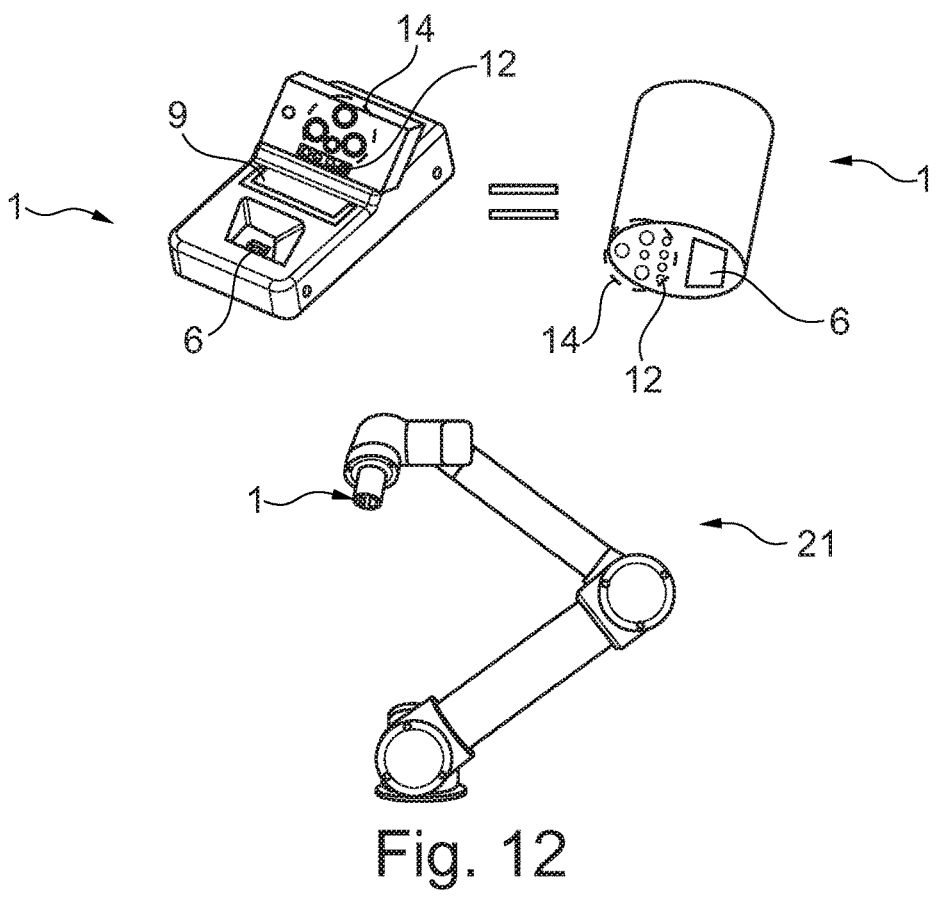
FIG. 12 is a representation of a robot arm with a smart port attached to or integrated into it.

FIG. 12 is a representation of a robot arm 21 with a smart port 1 attached to or integrated in it. FIG. 12 shows that the smart port 1 may also have a cylindrical shape, in which case the modules 6, 9, 12, 14 and 16 are integrated in one end face. The cylindrical smart port 1 is fixed/attached to one end of the robot arm 21 and is provided to recognize/detect medical products 2.

Figure 13:
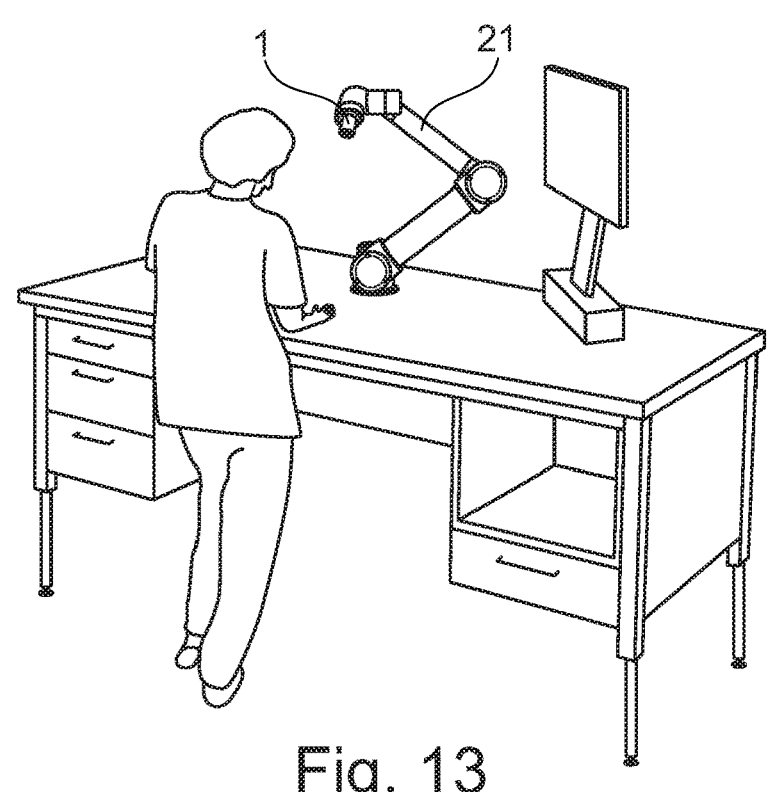
FIG. 13 is a representation of the robot arm in operation.

FIG. 13 is a representation of the robot arm 21 in operation.

Figure 14:
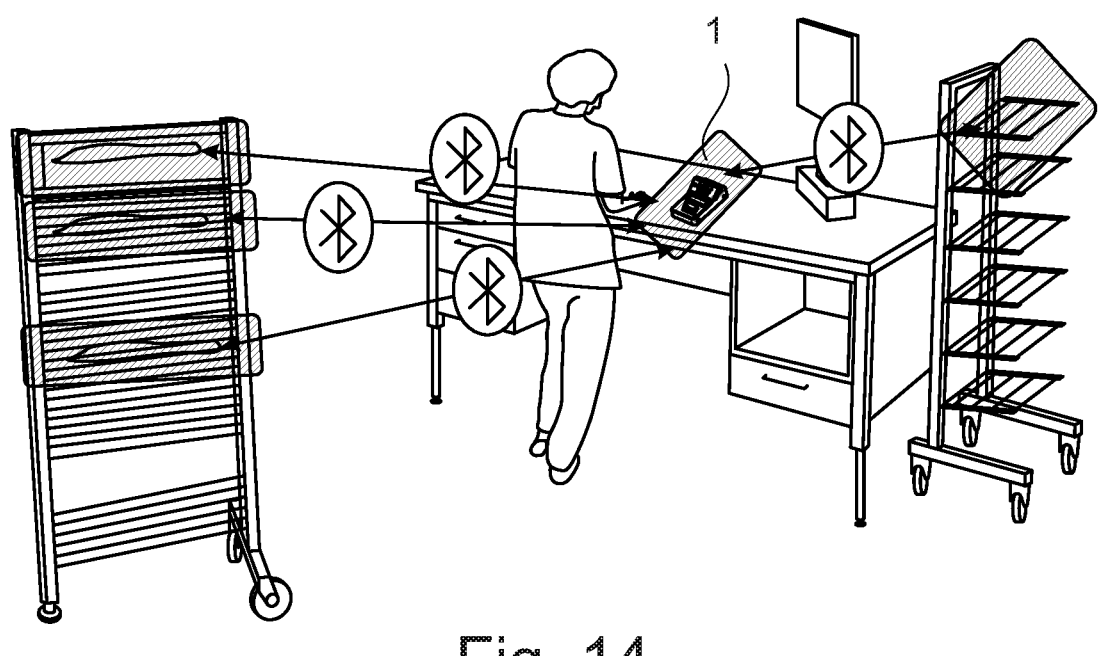
FIG. 14 is a representation of the communication connections of the smart port in operation.

FIG. 14 is a representation of the communication connections 28 of the smart port 1 in operation.

Figures 15, 16:
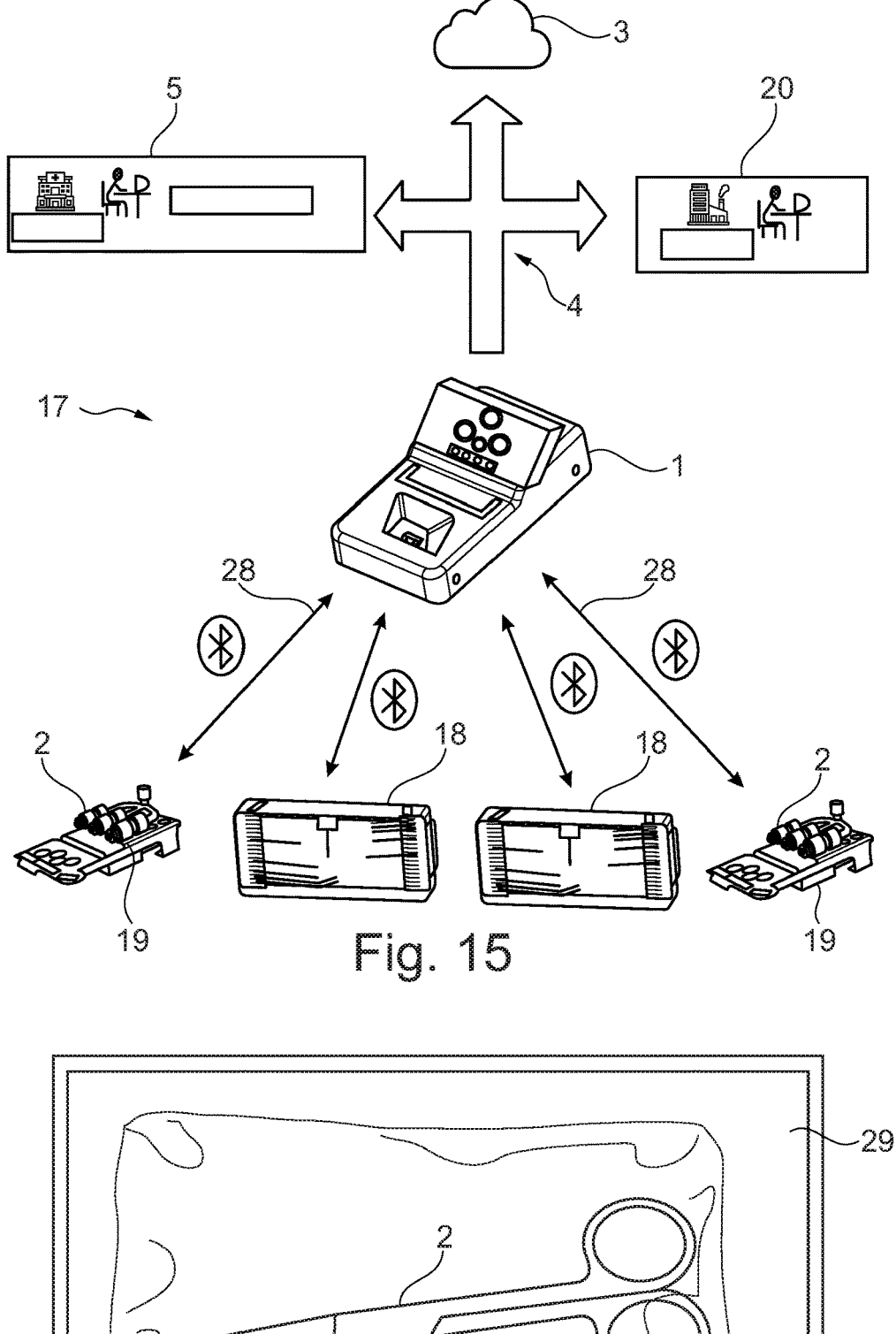
FIG. 15 is a representation of the system with a smart port, a sieve basket, and an instrument data management system of the customer, a cloud and an instrument data management system of the manufacturer.
FIG. 16 is the representation of a medical product in sterile packaging.

FIG. 15 is a representation of the system with a smart port 1, a sieve basket 18 and instrument holders 19 insertable therein, which hold the medical products 2, wherein the smart port 1 is provided and configured to read out data and information of the at least one medical product 2 in the sieve basket 18 and/or in the instrument holders 19 and to transmit them to an instrument data management system of the customer 5, a cloud 3 and/or to an instrument data management system of the manufacturer 20 for further processing. FIG. 15 furthermore shows the communication connections 28 via Bluetooth between the medical products 2 and the sieve baskets 18.

FIG. 16 is the representation of a medical product 2 in the form of a pair of scissors in a sterile packaging 29, which can be scanned without opening the sterile barrier.

The invention claimed is:

1. A system with a smart port, wherein the smart port is configured to:

A. read out data and information, in a sieve basket and/or instrument holder, of at least one medical product and to transmit the data and information to an instrument data management system of a customer, to a cloud and/or to an instrument data management system of a manufacturer for further processing, wherein the smart port defines a space around the smart port in which the at least one medical product is readable, wherein the smart port comprises a plurality of modules that are separate, combinable, and have different detection technologies to detect and read out the data and information of the at least one medical product, the plurality of modules comprising at least a first module configured with an optical detection technology and a second module configured with a radio detection technology;

B. detect the at least one medical product and to send a signal within a predetermined and/or predefined time window, wherein the signal is provided to log an assignment with a detection of the medical product as being correct or incorrect and C. compare the optical detection technology and the radio detection technology with each other within the predefined time window in order to confirm that the assignment is correct.

2. The system according to claim 1, wherein the predefined time window is within 2 to 3 seconds.

3. The system according to claim 1, wherein the smart port is configured to output at least two different feedback signals to recognize a correct assignment and an incorrect assignment.

4. The system according to claim 1, further configured to load the data into a cloud based infrastructure and to communicate with the instrument data management system of the customer and/or the instrument data management system of the manufacturer via an interface.

5. The system according to claim 4, wherein the smart port functions as a data collector configured to save the data on a non-volatile memory until the data is retrieved.

6. The system according to claim 1, wherein the first module is configured to read a data matrix code and/or a barcode that is configured to be applied to the at least one medical product and to be readable.

7. The system according to claim 1, wherein the second module is configured to read an RFID tag that is configured to be accommodated in the at least one medical product and to be readable and/or writable.

8. The system according to claim 7, wherein the second module operates in a frequency range of HF, UHF and/or SHF.

9. The system according to claim 1, wherein the plurality of modules further comprises a third module configured to perform surface scanning of the at least one medical product.

10. The system according to claim 1, wherein the plurality of modules further comprises a fourth module configured to save at least one image of the at least one medical product.

11. The system according to claim 1, wherein one of the plurality of modules is configured to recognize the at least one medical product based on a geometry and to compare the geometry with a target state of the at least one medical product.

12. The system according to claim 1, wherein the plurality of modules further comprises a fifth module configured to save the data via color differences.

13. The system according to claim 1, wherein the smart port is provided with an apparatus with artificial intelligence for recognizing and evaluating the at least one medical product based on a geometry of the at least one medical product.

14. The system according to claim 1, wherein the system is configured to detect and read the at least one medical product in a sterile goods cycle.

15. A system with a smart port, wherein the smart port is configured to:

A. read out data and information of at least one medical product and to transmit the data and information to an instrument data management system of a customer, to a cloud and/or to an instrument data management system of a manufacturer for further processing, wherein the smart port defines a space around the smart port in which the at least one medical product is readable, wherein the smart port comprises a plurality of modules that are separate, combinable, and have different detection technologies to detect and read out the data and information of the at least one medical product, the plurality of modules comprising at least a first module configured with an optical detection technology, a second module configured with a radio detection technology, and a third module configured with a LIDAR technology;

B. detect the at least one medical product and to send a signal within a predetermined and/or predefined time window, wherein the signal is provided to log an assignment with a detection of the medical product as being correct or incorrect; and C. compare the optical detection technology, the radio detection technology and the LIDAR technology with each other within the predefined time window in order to confirm that the assignment is correct.

* * * * *